United States Patent [19]

Lyle et al.

[11] Patent Number: 5,179,128

[45] Date of Patent: Jan. 12, 1993

[54] COSMETIC COMPOSITION FOR REMOVING MAKE-UP

[75] Inventors: Ian G. Lyle, Aston Park, Great Britain; Masaaki Nagase, Tokyo, Japan

[73] Assignee: Chesebrough-Pond's USA Co., Greenwich, Conn.

[21] Appl. No.: 766,991

[22] Filed: Sep. 27, 1991

[30] Foreign Application Priority Data

Oct. 2, 1990 [GB] United Kingdom ............... 9021417

[51] Int. Cl.$^5$ ................ A61K 7/02; A61K 7/26; A61K 7/48

[52] U.S. Cl. .................. 252/165; 514/847; 514/846; 252/166; 252/174.11; 252/174.21

[58] Field of Search ............... 514/846, 847, 845, 777

[56] References Cited

U.S. PATENT DOCUMENTS

| | | | |
|---|---|---|---|
| 3,934,003 | 1/1976 | Tuma et al. | 514/777 |
| 4,250,193 | 2/1981 | Ochiai et al. | 514/777 |
| 4,252,826 | 2/1981 | Boelle et al. | 514/777 |
| 4,375,465 | 3/1983 | Drakoff | 514/777 |
| 4,376,789 | 3/1983 | Lowicki et al. | 514/777 |
| 4,970,220 | 11/1990 | Chaussee | 514/846 |
| 5,030,374 | 7/1991 | Tranner | 514/846 |

FOREIGN PATENT DOCUMENTS

| | | | |
|---|---|---|---|
| 213827 | 3/1987 | European Pat. Off. | 424/47 |
| 217105 | 4/1987 | European Pat. Off. | 514/844 |

*Primary Examiner*—Dale R. Ore
*Attorney, Agent, or Firm*—Milton L. Honig

[57] ABSTRACT

A cleansing composition suitable for topical application to human skin to remove make-up, the composition comprising:

A. a surfactant system comprising:
  i) a water-dispersible anionic alkali metal $C_{10}$–$C_{18}$ alkylether carboxylate; and
  ii) a water-dispersible nonionic partially esterified polyol; and
B. an oil substance chosen from hydrocarbons, esters of a higher alcohol and a higher fatty acid, fatty alcohols, fatty acids, triglycerides, oils or fats of animal and vegetable origin, cholesterol fatty acid esters, perfume oils and mixtures thereof.

12 Claims, No Drawings

COSMETIC COMPOSITION FOR REMOVING MAKE-UP

FIELD OF THE INVENTION

The invention relates to a cleansing composition suitable for topical application to human skin, more particularly to an oil-based cleansing composition, substantially free from added water, containing a special surfactant system for removal of make-up from the skin.

BACKGROUND AND PRIOR ART

The topical application to human skin, in particular to the face of substances for cosmetic purposes, such as make-up, has since time immemorial been and still is, an art form employed particularly by women, as part of a daily or periodical ritual or routine to embellish or beautify their appearance in the eyes of the beholder and/or to enhance confidence, to enable them more readily to face each day. Topical application of make-up, particularly to exposed areas of the skin, can also provide some protection from the elements, such as the sun, the wind and the rain, where otherwise the skin damage or accelerated skin ageing can occur.

Make-up, once applied to the skin, has conventionally only a limited life, and must be removed from time to time, in order to replenished it anew. To habitual make-up users, this is a daily or twice daily activity.

The removal of make-up, particularly waxed based make-up such as lipstick and mascara, presents a special problem in that it can adhere strongly to the skin and can resist ordinary washing with soap and water, or with mild detergent products especially formulated for use on delicate skin areas, such as the face. Scrubbing of the skin to remove make-up can be successful, but damage to the underlying sensitive skin can result.

Oil based cleansing products such as 'cold cream' have been recommended for cleaning make-up from the skin, but the resultant oil residue consisting of a mixture of solubilised make-up and excess cleanser is difficult to remove either by wiping off or by rinsing with water.

A mild, skin-cleansing, non-foaming mousse forming aqueous emulsion is described by Procter & Gamble in EP 0 213 827. The mousse comprises a nonionic surfactant, such as an ethoxylated nonionic surfactant or a partially esterified polyol, an emollient such as a mineral oil or vegetable oil, a moisturiser such as glycerin or sorbitol and a water soluble gaseous propellant such as carbon dioxide and nitrogen.

A lamella type single phase liquid crystal composition prepared from a hydrophilic nonionic surfactant, a water-soluble substance having a hydroxyl group, and oil substance and water has been proposed by Kao in EP 217 105 as a system suitable for cleansing the skin.

SUMMARY OF THE INVENTION

Attempts to employ aqueous systems, such as those proposed by Procter & Gamble and by Kao, as well as other conventional body cleansing products such as "cold cream", in the removal of tenacious make-up, have met with only partial success, and accordingly, there remains a problem of complete removal of make-up without resort to solvents or physical abrasion that might cause damage to the skin.

We have now discovered that by selecting a special surfactant system and an oil substance, without the addition of a significant amount of water, a composition is obtained which has excellent make-up removal properties, and which can be readily removed from the skin by wiping or by rinsing with water.

DEFINITION OF THE INVENTION

Accordingly, the invention provides a cleansing composition suitable for topical application to human skin to remove make-up, the composition comprising:

A. a surfactant system comprising:
  i) a water-dispersible anionic alkali metal $C_{10}$–$C_{18}$ alkylether carboxylate; and
  ii) a water-dispersible nonionic partially esterified polyol; and
B. an oil substance chosen from hydrocarbons, esters of a higher alcohol and a higher fatty acid, fatty alcohols, fatty acids, triglycerides, oils or fats of animal and vegetable origin, cholesterol fatty acid esters, perfume oils and mixtures thereof.

DISCLOSURE OF THE INVENTION

The cleansing composition according to the invention which is substantially free from added water and comprises a special anionic surfactant, a special nonionic surfactant and an oil substance.

The Anionic Surfactant

The cleansing composition according to the invention comprises, as an anionic surfactant, a water-dispersible alkali metal $C_{10}$–$C_{18}$ alkylether carboxylate.

A preferred example of the anionic surfactant is sodium polyoxyethylene tridecylether carboxylate [6 EO], (e.g. UNISAFE ECT ex Nippon Oil & Fat).

The amount of the anionic surfactant present in the composition of the invention is from 1% to 25%, preferably from 5% to 15% by weight.

The Nonionic Surfactant

The cleansing composition according to the invention also comprises, as a nonionic surfactant, a partially esterified polyol.

A preferred example of the nonionic surfactant is decaglyceryl monolaurate, (e.g. NIKKOL ex Nippon Surfactant Kogyo).

The amount of the nonionic surfactant present in the composition of the invention is from 0.5% to 20%, preferably from 1% to 10% by weight.

The Oil Substance

The cleansing composition according to the invention comprises an oil substance chosen from hydrocarbons, esters of a higher alcohol and a higher fatty acid, fatty alcohols, fatty acids, triglycerides, oil or fats of animal and vegetable origin, cholesterol fatty acid esters, perfume oils and mixtures thereof.

By "oil substance" we mean a cosmetically acceptable substantially water-immiscible liquid.

Examples of oils for use in the composition according to the invention include:

saturated or unsaturated, straight or branched chain $C_{8-22}$ alkane esters, for example
  isopropylmyristate (e.g. ESTOL 1514, ex Unichema)
  hexyl laurate (e.g. CETIOL A, ex Henkel)
  methyl laurate (e.g. ESTOL 1502, ex Unichema)
  2-ethylhexyl palmitate (e.g. GLYCO 0-300, ex Glyco)
  2-octyldodecyl myristate (e.g. MOD, ex Nippon Oils & Fats)

propyleneglycol dicaprylate/caproate (e.g. ESTOL 1526, ex Unichema)

isopropylpalmitate (e.g. ESTOL 1517, ex Unichema)

decyloleate (e.g. CETIOL V, ex Henkel)

triglycerides such as glyceryl tri-caprylate/caprate (e.g. ESTOL 1527, ex Unichema)

glyceryl tri-isostearate (e.g. PRISORINE, ex Unichema)

glyceryl tri-(2-ethylhexanoate) (e.g. PANACEAT 800B ex Nippon Oil & Fat), and hydrocarbons, such as liquid petrolatum (e.g. CARNATION ex Witco).

Preferred oil substances according to the invention are synthetic triglycerides, especially those having branched acyl chains, in particular glyceryl tri-(2-ethylhexanate).

The amount of oil substance present in the composition of the invention is from 10% to 90%, preferably from 20% to 80% by weight.

Compositions containing less than 10% by weight of oil substance tend to be poor at removing make-up from human skin, while those containing more than 90% by weight of the oil substance are difficult to rinse from the skin with water and can leave the skin in a greasy state after use. Furthermore their efficacy at removing make-up is not further enhanced.

OTHER INGREDIENTS

Cosmetic Adjuncts

The composition according to the invention can optionally comprise cosmetic adjuncts, examples f which are:

preservatives, such as:
  p-hydroxybenzoate esters
  2-bromo2-nitropropane-1,3-diol
  salicylic acid
antioxidants, such as:
  butylated hydroxy toluene
  butylated hydroxy anisole
  tocopherol
skin conditioners, such as
  Polyquaternium 10
  PEG-7 glyceryl cocoate
emulsion stabilisers (co-emulsifiers), such as:
  cetyl alcohol
  glyceryl mono/distearate
  stearic acid
humectants, such as:
  glycerol
  propylene glycol
  dipropylene glycol
  sorbitol
  2-pyrrolidone-5-carboxylate
  polyethyleneglycol (e.g. PEG 200-600)
thickeners, such as
  carbomers
  xanthan gum
  hectorite
  fumed silica
  hydrotalcites
  waxes, such as bees wax.

A preferred type of thickener is hydrotalcite thickeners, such as for example aluminum magnesium hydroxystearates, as described in DE 3731919 (Giulini). Preferably, the hydrotalcites are modified with fatty acids, more preferably branched chain fatty acids, most preferably 2-ethyl hexanoate or isostearate.

In a preferred embodiment of the invention, the hydrotalcite is present at a concentration of from 1-5% by weight of the composition. Consequently the hydrotalcite may be added to the composition during manufacture as a gel, comprising for example 10-20% hydrotalcite in an oil which is a preferred component of the make-up removal composition.

It is found that compositions containing hydrotalcite as a thickening agent demonstrate shear thinning on application to the skin, and therefore spread more easily over the skin.

Further preferred thickeners according to the invention are waxes, especially bees wax. If waxes are used in the composition, preferably they are used at a level of 10-20% by weight of the composition, more preferably 12-18% by weight of the composition.

plant extracts, such as
  Aloe vera
  cornflower
  witch hazel
  elderflower
  cucumber
colourants and perfumes.

Cosmetic adjuncts can form up to 50% by weight of the composition and can conveniently form the balance of the composition.

Process for Preparing the Composition

The invention also provides a process for the preparation of a cleansing composition for topical application to skin which comprises the step of blending together an oil substance, a special anionic surfactant and a special nonionic surfactant, as herein defined, to form the composition.

Use of the Composition

The composition according to the invention is intended primarily as a product for topical application to cleanse human skin, particularly to remove make-up from the face and other parts of the body.

In use, a small quantity of the composition, for example from 1 to 5 ml, is applied to the affected area of skin. If necessary, the composition is then spread over and/or rubbed onto the skin using the hand or fingers or a suitable device, in order to effect a cleansing action.

The emulsified residue can then easily be removed by wiping off with a tissue or by rinsing with water.

PRODUCT FORM AND PACKAGING (US)

The topical skin cleansing composition of the invention can be formulated as a liquid or gel having a viscosity usually of from 10 to 2,000 mPas, as measured with a Brookfield RVT viscometer using spindle 3 at 25° C. The composition can be packaged in a suitable container, from which it can be dispensed directly onto the skin or via an applicator.

The invention accordingly also provides a closed container containing the cosmetically acceptable cleansing composition as herein defined.

The invention also accordingly provides for a method of treatment for the human skin to remove make-up using a composition comprising:

A. a surfactant system comprising:
  i) a water-dispersible anionic alkali metal $C_{10}$–$C_{18}$ alkylether carboxylate; and ii) a water-dispersable nonionic partially esterified polyol; and B. an oil substance chosen from hydrocarbons, esters of a higher alcohol and a higher fatty acid, fatty alcohols, fatty acids, triglycerides, oils or fats of animal and vegetable origin, cholesterol fatty acid esters, perfume oils and mixtures thereof.

Evidence to Demonstrate Ability of the Composition in Removing Make-up From Skin The subjective Lipstick Removal Test The subjective test is performed by human volunteers, to whose forearms is applied a lipstick 'cross' An attempt is then made to remove the 'cross' by following a standard cleansing procedure using a variety of products, some compositions in accordance with the invention and some outside the monopoly claimed.

Materials

The lipstick chosen for this test is Cutex Lip Moist 040. The cleansing products had the following formulation:

| Ingredients | % w/v |
|---|---|
| Special anionic surfactant | 10 |
| Special nonionic surfactant | 2 |
| Special oil | 88 |

Method

A lipstick 'cross' (3 cm by 3 cm) was applied to the left forearm of each right handed volunteer (or vice versa if left handed).

A 5 ml dose of the cleaning product was applied directly to the lipstick cross and rubbed in for 10 seconds.

The arm was finally rinsed in luke-warm water and removal of the lipstick estimated subjectively as follows:

| 0 | none removed |
|---|---|
| 1 | poor removal |
| 2 | satisfactory removal |
| 3 | complete removal |

Results

The results of a series of cleansing tests showed that the composition as tested, which was in accordance with the invention, showed excellent lipstick removal properties.

EXAMPLES

The invention is further exemplified by the following examples, which illustrate cleansing compositions according to the invention.

EXAMPLE 1

| Ingredients | % w/w |
|---|---|
| Sodium polyoxyethylene tridecyl carboxylate (6 EO) | 10 |
| Decaglyceryl monolaurate | 2 |
| Liquid Petrolatum | 20 |
| Triglyceride 2-ethylhexanoate | 68 |

EXAMPLE 2

| Ingredients | % w/w |
|---|---|
| Sodium polyoxyethylene tridecyl carboxylate (6 EO) | 10 |
| Decaglyceryl monolaurate | 2 |
| Liquid Petrolatum | 20 |
| Triglyceride 2-ethylhexanoate | 65.5 |
| Hydrotalcite (aluminum magnesium hydroxystearate) | 2.5 |

Preferably the composition according to Example 2 is made up by blending together the sodium polyoxyethylene tridecyl carboxylate, the decaglyceryl monolaurate, the liquid petrolatum, and part of the triglyceride 2-ethylhexanoate. To this is added the hydrotalcite, as a 15% w/w gel composition in the remainder of the triglyceride 2-ethylhexanoate.

We claim:

1. A cleansing composition for topical application to human skin to remove make-up, the composition comprising:

A.
   i) from 1% to 25% of a water-dispersible anionic alkali metal $C_{10}$–$C_{18}$ alkyl ether carboxylate; and
   ii) from 0.5% to 20% of a water-dispersible nonionic partially esterified polyol; and
b. from 10% to 90% of an oil substance selected from the group consisting of hydrocarbons, esters of a higher alcohol and a higher fatty acid, fatty alcohols, fatty acids, triglycerides, animal oils, vegetable oils, animal fats, vegetable fats, cholesterol fatty acid esters, perfume oils and mixtures thereof.

2. A composition according to claim I, in which the anionic surfactant is sodium polyoxyethylene tridecylether carboxylate [6 EO].

3. A composition according to claim 1, in which the nonionic surfactant is decaglyceryl monolaurate.

4. A composition according to claim 1, in which the oil substance is a triglyceride oil.

5. A composition according to claim 4, in which the triglyceride oil comprises one or more branched chain ester groups.

6. A composition according to claim 5, in which the triglyceride oil is glyceryl tri(2-ethylhexanoate).

7. A composition according to claim 1, in which the oil substance is liquid petrolatum.

8. A composition according to claim 1 additionally comprising a thickener.

9. A composition according to claim 8 wherein the thickener is a hydrotalcite.

10. A composition according to claim 1, which comprises

A.
   i) from 1 to 25% by weight of sodium polyoxyethylene tridecylether carboxylate;
   ii) from 0.5 to 20% by weight of decaglyceryl monolaurate; and
b.
   i) from 10 to 90% by weight of glyceryl tri(2-ethylhexanoate).

11. A composition according to claim 10 additionally comprising 1–5% by weight of a hydrotalcite compound.

12. Method of treatment of the human skin to remove make-up using a composition comprising:

a.
   i) from 1% to 25% of a water-dispersible anionic alkali metal $C_{10}$–$C_{18}$ alkyl ether carobxylate; and
   ii) from 0.5% to 20% of a water-dispersible nonionic partially esterified polyol; and
B. from 10% to 90% of an oil substance selected from the group consisting of hydrocarbons, esters of a higher alcohol and a higher fatty acid, fatty alcohols, fatty acids, triglycerides, animal oils, vegetable oils, animal fats, vegetable fats, cholesterol fatty acid esters, perfume oils and mixtures thereof.

* * * * *